US012678441B2

(12) United States Patent　　(10) Patent No.:　US 12,678,441 B2
Mishra et al.　　　　　　　　　　(45) **Date of Patent:　*Jul. 14, 2026**

(54) METHOD OF MAKING COMPOSITION INCLUDING ENCAPSULATED CAFFEINE

(71) Applicant: Altria Client Services LLC, Richmond, VA (US)

(72) Inventors: Munmaya K. Mishra, Manakin Sabot, VA (US); Gerd Kobal, Sandy Hook, VA (US)

(73) Assignee: Altria Client Services LLC, Richmond, VA (US)

( * ) Notice: Subject to any disclaimer, the term of this patent is extended or adjusted under 35 U.S.C. 154(b) by 1026 days.

This patent is subject to a terminal disclaimer.

(21) Appl. No.: 17/332,277

(22) Filed: May 27, 2021

(65) Prior Publication Data

US 2021/0283137 A1　　Sep. 16, 2021

Related U.S. Application Data

(62) Division of application No. 16/215,081, filed on Dec. 10, 2018, now Pat. No. 11,020,401, which is a division of application No. 14/206,008, filed on Mar. 12, 2014, now Pat. No. 10,149,850.

(60) Provisional application No. 61/794,491, filed on Mar. 15, 2013.

(51) Int. Cl.

| | |
|---|---|
| *A61K 31/522* | (2006.01) |
| *A23L 2/52* | (2006.01) |
| *A23L 23/00* | (2016.01) |
| *A23L 33/105* | (2016.01) |
| *A23P 10/30* | (2016.01) |
| *A24B 13/00* | (2006.01) |
| *A24B 15/28* | (2006.01) |
| *A23L 7/126* | (2016.01) |

(52) U.S. Cl.
CPC .............. *A61K 31/522* (2013.01); *A23L 2/52* (2013.01); *A23L 23/00* (2016.08); *A23L 33/105* (2016.08); *A23P 10/30* (2016.08); *A24B 13/00* (2013.01); *A24B 15/283* (2013.01); *A23L 7/126* (2016.08); *A23V 2002/00* (2013.01); *A23V 2250/02* (2013.01); *A23V 2250/2108* (2013.01)

(58) Field of Classification Search
None
See application file for complete search history.

(56) References Cited

U.S. PATENT DOCUMENTS

| | | | |
|---|---|---|---|
| 3,064,311 | A | 11/1962 | Bain |
| 4,521,438 | A | 6/1985 | Zeller et al. |
| 4,547,378 | A | 10/1985 | Saleeb et al. |
| 4,767,634 | A | 8/1988 | Kaleda et al. |
| 4,946,701 | A | 8/1990 | Tsai et al. |
| 5,336,513 | A | 8/1994 | Riemer |
| 6,165,516 | A | 12/2000 | Gudas et al. |
| 6,845,777 | B2 | 1/2005 | Pera |
| 7,125,564 | B2 | 10/2006 | Chen et al. |
| 7,150,880 | B2 | 12/2006 | Howard et al. |
| 7,371,841 | B2 | 5/2008 | Julius et al. |
| 7,851,006 | B2 | 12/2010 | Bingley et al. |
| 7,950,399 | B2 | 5/2011 | Winterson et al. |
| 7,980,251 | B2 | 7/2011 | Winterson et al. |
| 2002/0197381 | A1 | 12/2002 | Burgard |
| 2003/0049208 | A1 | 3/2003 | Ream et al. |
| 2006/0204551 | A1 | 9/2006 | Manley et al. |
| 2007/0031539 | A1 | 2/2007 | Calton, Jr. |
| 2007/0186941 | A1* | 8/2007 | Holton, Jr. ........... A24B 15/283 |
| | | | 131/347 |
| 2007/0196496 | A1 | 8/2007 | Farber et al. |
| 2008/0152763 | A1 | 6/2008 | Bohannon |
| 2008/0210249 | A1 | 9/2008 | Luzenberg |
| 2008/0276948 | A1 | 11/2008 | Gedevanishvili et al. |
| 2009/0025741 | A1 | 1/2009 | Crawford et al. |
| 2009/0186127 | A1 | 7/2009 | Krumhar et al. |
| 2010/0298258 | A1 | 11/2010 | Mitchell |
| 2010/0300464 | A1* | 12/2010 | Gee ........................ A24F 23/00 |
| | | | 131/275 |
| 2011/0123680 | A1 | 5/2011 | Tanaka et al. |
| 2011/0159141 | A1 | 6/2011 | Luo et al. |

FOREIGN PATENT DOCUMENTS

| | | | |
|---|---|---|---|
| EP | 2074893 A1 | 7/2009 | |
| FR | 2923990 A1 | 5/2009 | |
| JP | H-0227945 A | 1/1990 | |
| JP | 2002/330735 A | 11/2002 | |
| WO | WO-98/23165 A1 | 6/1998 | |

(Continued)

OTHER PUBLICATIONS

Tomar et al. (Tobacco Control 1997;6:219-225).*
Trask et al., Crystal Growth & Design, 2005, vol. 5, No. 3, pp. 1013-1021.
Liu et al., Journal of Pharmaceutical Sciences, vol. 96, pp. 927-934, 2007.
Cesaro et al., The Journal of Physical Chemistry, vol. 80, No. 3, 1976.
Bucar et al., Chem. Commun., 2007, pp. 525-527.
Jun. 11, 2014 International Search Report and Written Opinion issued in PCT/US2014/024663.
"Encapsulated Caffeine & Vitamins", http://www.microteklabs.com/encapsulated-caffeine-and-vitamins.html, Feb. 1, 2012, XP055118563.
International Preliminary Report on Patentability issued Sep. 15, 2015 in International Application No. PCT/US2014/024663.

(Continued)

*Primary Examiner* — Anna R Falkowitz
*Assistant Examiner* — Garen Gotfredson
(74) *Attorney, Agent, or Firm* — Harness, Dickey & Pierce, P.L.C.

(57) ABSTRACT

The method includes forming encapsulated caffeine from a caffeine complex that includes caffeine and an organic acid in a 1:1 molar ratio, dispersing the encapsulated caffeine throughout at least a portion of a base composition, the encapsulated caffeine being included in an amount sufficient to release 50 mg to 200 mg of caffeine when consumed, and adding at least one pH adjusting agent to the base composition to maintain a pH of the base composition within a range between 2 and 5.

22 Claims, 1 Drawing Sheet

(56)                    References Cited

FOREIGN PATENT DOCUMENTS

| WO | WO-00/13523 A1 | 3/2000 |
| WO | WO-2008/045579 A1 | 4/2008 |
| WO | WO-2008/080005 A1 | 7/2008 |
| WO | WO-2008/119196 A1 | 10/2008 |
| WO | WO-2008/119197 A1 | 10/2008 |
| WO | WO-2011/011418 A1 | 1/2011 |
| WO | WO-2012/005349 A1 | 1/2012 |
| WO | WO-2013/063163 A1 | 5/2013 |

OTHER PUBLICATIONS

International Search Report and Written Opinion issued Jul. 7, 2014 in International Application No. PCT/US2014/025720.
TFG: The Food Guru: http://foodguru802.blogspot.com/2012/02energy-shots-are-they-healthy.html; published Feb. 10, 2012.
Burton, Published online Feb. 1, 2012, at https://springsoralhealth.wordpress.com/2012/02/01/ph-of-soft-drinks.
Examine.com, published online at least by Jan. 5, 2012 at http://web.archive.org/web/2012010500584 http://examine.com/supplements/Capsaicin/.
CSPI: published online at least by Jan. 24, 1998 at http://web.archive.org/web/19980124040618/http://www.cspinet.org/ne/cafchart.htm.
International Preliminary Report on Patentability issued Sep. 15, 2015 in International Application No. PCT/US2014/025720.

Non-Final Office Action issued Jun. 5, 2015 in U.S. Appl. No. 14/207,104.
Final Office Action issued Nov. 27, 2015 in U.S. Appl. No. 14/207,104.
Non-Final Office Action issued Apr. 20, 2016 in U.S. Appl. No. 14/207,104.
Final Office Action issued Sep. 15, 2016 in U.S. Appl. No. 14/207,104.
Non-Final Office Action issued Jan. 13, 2017 in U.S. Appl. No. 14/207,104.
Final Office Action issued May 3, 2017 in U.S. Appl. No. 14/207,104.
Non-Final Office Action issued Oct. 3, 2017 in U.S. Appl. No. 14/207,104.
Final Office Action issued Mar. 15, 2018 in U.S. Appl. No. 14/207,104.
Pre-Brief Appeal Conference Decision issued Jul. 30, 2018 in U.S. Appl. No. 14/207,104.
Examiner's Answer to Appeal Brief issued Dec. 21, 2018 in U.S. Appl. No. 14/207,104.
McKemy: TRP Ion Channel Function in Sensory Transduction and Cellular Signalling Cascades; Chapter 13TRPM8; The Cold and Menthol Receptor; Liedtke WB, Heller S. Editors. Boca Raton (FL); CRC Press Taylor & Francis; 2007.
"Genital Herpes" NEJM Resident 360 published on Aug. 18, 2016. https://resident360.nejm.org/content items/genital-herpes.
Microtek, Encapsulated Caffeine & Vitamins, <http://www.microteklabs.com/encapsulated-caffein-ad_vitamins.html> (Jan. 1, 2013; Printed May 16, 2014).
English translation of JP2008011834 (2008).

* cited by examiner

METHOD OF MAKING COMPOSITION INCLUDING ENCAPSULATED CAFFEINE

CROSS-REFERENCE TO RELATED APPLICATION

This application is a divisional of U.S. application Ser. No. 16/215,081, filed Dec. 10, 2018, which is a divisional of U.S. patent application Ser. No. 14/206,008, filed Mar. 12, 2014, issued as U.S. Pat. No. 10,149,850 on Dec. 11, 2018, which claims priority under 35 U.S.C. § 119(e) to U.S. provisional Application No. 61/794,491, filed on Mar. 15, 2013, the entire contents of each of which are incorporated herein by reference thereto.

BACKGROUND

Caffeine occurs naturally in tea, coffee, and chocolate, and is commonly added to soft drinks, energy drinks and some foods to provide a burst of energy to the consumer. In particular, energy drinks having high caffeine content are very popular. However, because of the bitter taste of caffeine, the high caffeine content of such energy drinks can be unappealing to consumers.

As such, energy drinks, foods, oral non-tobacco products and/or oral tobacco products having a relatively high caffeine content that does not have a bitter taste are desirable.

SUMMARY

In a preferred embodiment, a composition for human consumption comprises a predetermined quantity of a base composition and encapsulated caffeine dispersed throughout at least a portion of the base composition. The encapsulated caffeine is a caffeine complex including caffeine and an organic acid in about a 1:1 molar ratio. The organic acid can be a monocarboxylic acid, a dicarboxylic acid and/or a multi-carboxylic acid. Suitable organic acids are selected from the group consisting of caffeic acid, oxalic acid, malonic acid, maleic acid, succinic acid, glutaric acid, glutamic acid, adipic acid and combinations thereof. The encapsulated caffeine releases about 50 mg to about 200 mg of caffeine when consumed or about 100 mg to about 150 mg of caffeine when consumed. Preferably, the base composition has a pH of about 2 to about 5.

In one embodiment, the base composition comprises a liquid having a volume of about 200 mL to about 600 mL. The liquid is selected from the group consisting of water, vegetable juice, fruit juice and combinations thereof. The liquid is a carbonated liquid or a non-carbonated liquid. Alternatively, the base composition can be a food.

In the preferred embodiment, the composition also includes at least one additive selected from the group consisting of at least one flavorant, at least one viscosity increasing agent, at least one sweetener, at least one vitamin, at least one mineral, at least one nutraceutical, at least one colorant, at least one preservative, at least one sensate, at least one pH adjusting agent, or combination thereof. The at least one flavorant is included in the composition in an amount ranging from about 0.5% by weight based on the weight of the composition to about 25% by weight based on the weight of the composition. Moreover, the at least one pH adjusting agent is added to the composition in an amount sufficient to adjust and/or maintain the pH of the composition to a pH of about 2 to about 5.

In the preferred embodiment, the at least one viscosity increasing agent is selected from the group consisting of pectin, alginate, starch, hydroxypropyl methyl cellulose, guar gum and combinations thereof and wherein the at least one viscosity increasing agent is included in the composition in an amount ranging from about 0.5% by weight based on the weight of the composition to about 5% by weight based on the weight of the composition. Also, the at least one sweetener is included in the composition in an amount ranging from about 0.01% to about 15% by weight based on the weight of the composition. Moreover, the at least one sweetener is selected from the group consisting of sucrose, fructose, dextrose, high fructose corn syrup, high maltose syrup, sugar alcohols, sugar naturally present in fruit juices and combinations thereof.

In another embodiment, an oral pouch product comprises a porous pouch wrapper, an inner botanical filling material contained within the pouch wrapper and encapsulated caffeine dispersed throughout at least a portion of the oral pouch product. The encapsulated caffeine is a caffeine complex including caffeine and an organic acid in about a 1:1 molar ratio. The organic acid can be a monocarboxylic acid, a dicarboxylic acid and/or a multi-carboxylic acid. Suitable organic acids are selected from the group consisting of caffeic acid, oxalic acid, malonic acid, maleic acid, succinic acid, glutaric acid, glutamic acid, adipic acid and combinations thereof. The encapsulated caffeine releases about 50 mg to about 200 mg of caffeine per oral pouch product when held in a consumer's mouth over a period of about 1 minute to about 40 minutes.

Preferably, the botanical material includes tobacco or non-tobacco plant material and wherein the encapsulated caffeine is dispersed throughout the botanical material. Moreover, the oral pouch product can also include a coating on a surface of the porous pouch wrapper. The encapsulated caffeine is dispersed throughout the coating.

In yet another embodiment, a method of making a composition for human consumption comprises dispersing encapsulated caffeine throughout at least a portion of a base composition. The encapsulated caffeine is a caffeine complex including caffeine and an organic acid in about a 1:1 molar ratio. The organic acid can be a monocarboxylic acid, a dicarboxylic acid and/or a multi-carboxylic acid. Suitable organic acids are selected from the group consisting of caffeic acid, oxalic acid, malonic acid, maleic acid, succinic acid, glutaric acid, glutamic acid, adipic acid and combinations thereof. The encapsulated caffeine is included in an amount sufficient to release about 50 mg to about 200 mg of caffeine when consumed.

In the preferred embodiment, the method can also include adding one or more additives selected from the group consisting of at least one flavorant, at least one viscosity increasing agent, at least one sweetener, at least one vitamin, at least one mineral, at least one nutraceutical, at least one colorant, at least one preservative, or combination thereof. The method can also include adding at least one pH adjusting agent operable to adjust and/or maintain the composition at a pH of about 2 to about 5. Preferably, the composition is a drink, a food, an oral tobacco pouch product or an oral non-tobacco pouch product.

DETAILED DESCRIPTION

Figure 1:
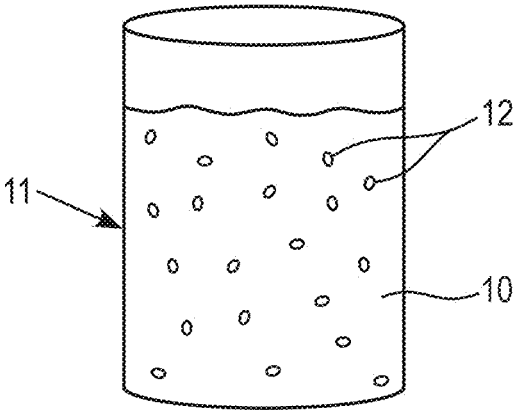
FIG. 1 is an illustration of an energy drink having encapsulated caffeine dispersed therein.
Figure 2:
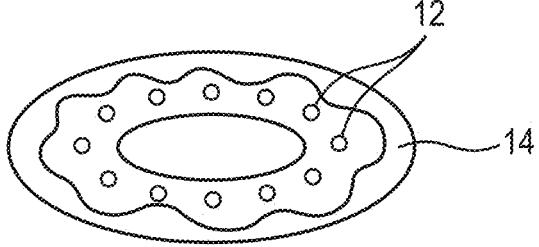
FIG. 2 is an illustration of an energy food including encapsulated caffeine therein.

Energy drinks and food products containing a relatively high level of caffeine are very popular. The relatively high caffeine content provides a burst of energy to the consumer because caffeine stimulates the nervous system. Such drinks and foods can also include vitamins, amino acids, herbal extracts, choline derivatives and other ingredients, which are believed to energize the consumer of the drinks or foods.

Caffeine, also known as 1,3,7-trimethyl xanthine, is a white, odorless, bitter tasting substance. Caffeine occurs naturally in tea, coffee, and chocolate, and is commonly added to soft drinks, energy drinks and some foods. However, because of the bitter taste of caffeine, the flavor of drinks or foods having a relatively high caffeine content can be unappealing.

To overcome the bitterness, large amounts of sweeteners, acids and flavors are often added to energy drinks and foods. Despite the addition of such ingredients, the energy foods and drinks typically still have a bitter taste.

As such, compositions for human consumption such as energy drinks and foods, and oral products such as oral non-tobacco products and/or oral tobacco products including encapsulated caffeine are provided herein. The compositions for human consumption include relatively high amounts of caffeine without the bitter taste associated therewith. Such compositions for human consumption not having a bitter taste are formed using encapsulated caffeine as opposed to pure caffeine, which is commonly used to form energy drinks or foods.

As used herein, the term "encapsulated caffeine" refers to caffeine complexes including about a 1:1 molar ratio of caffeine and an organic acid. The organic acid can be a monocarboxylic acid, a dicarboxylic acid and/or a multi-carboxylic acid. Suitable organic acids are selected from the group consisting of caffeic acid, oxalic acid, malonic acid, maleic acid, succinic acid, glutaric acid, glutamic acid, adipic acid and combinations thereof. In a preferred embodiment, the organic acid is caffeic acid. Also preferably, the caffeine complex forms crystals which can be dispersed throughout the composition.

In a preferred embodiment, the encapsulated caffeine is in the form of a caffeine complex. Caffeine is often obtained by extraction from coffee, tea, and chocolate. One method of extraction involves the formation of caffeine complexes, which are filtered out to create decaffeinated coffee and tea. Caffeine complexes can be formed by contacting a coffee or tea extract with an organic acid, such as caffeic acid, which forms the caffeine complex upon contact. Other suitable organic acids include organic acids selected from the group consisting of oxalic acid, malonic acid, maleic acid, succinic acid, glutaric acid, glutamic acid, adipic acid and combinations thereof. The caffeine complexes include about a 1:1 molar ratio of caffeine and the organic acid (e.g., caffeic acid). Typically, the caffeine complexes can then be discarded. Alternatively, the caffeine can be recovered from the caffeine complex and purified for use in other products. However, as described herein, the caffeine complexes can be collected and included in energy drinks, foods, oral non-tobacco products and/or oral tobacco products having relatively minimal bitter taste as compared to energy drinks, foods, oral non-tobacco products and/or oral tobacco products including pure caffeine.

Formation of the caffeine complex and recovery and purification of caffeine can be performed by dissolving the caffeine complex in a solvent as described in U.S. Pat. Nos. 4,521,438; 4,767,634; and 4,547,378; the entire content of each of which is incorporated herein by reference thereto.

In the preferred embodiment, the composition for human consumption can be formed by combining the encapsulated caffeine with a base composition. Optionally, the composition for human consumption can also include one or more additives as described in detail below.

The compositions for human consumption have a relatively high caffeine content so as to provide a consumer with a burst of energy. Moreover, the compositions for human consumption contain about 50 mg to about 200 mg of caffeine or about 75 mg to about 175 mg of caffeine (e.g., 100 mg to about 150 mg of caffeine) so as to provide a burst of energy to the consumer. Preferably, the composition provides a single serving of a food, drink, oral tobacco product or oral non-tobacco product. A single serving of food can have a weight of about 5 g to about 450 g. A single serving of drink is about 200 mL to about 600 mL. A single serving of an oral pouch product includes one oral pouch product formed as described herein.

As used herein, the term "base composition" refers to at least a portion of foods, liquids, oral tobacco products and/or oral non-tobacco products to which the encapsulated caffeine can be added.

Suitable liquids include, without limitation, water, fruit juices, vegetable juices and combinations thereof. The liquids can include any suitable drinkable liquids, which can be carbonated or still. Preferably, the liquid is non-alcoholic and can contain additives such as flavors, colors, sweeteners and other additives as described herein.

Preferably, the encapsulated caffeine 12 is dispersed throughout a liquid 10 to form an energy drink 11 as shown in FIG. 1.

Suitable foods include, without limitation, any solid or liquid food product to which the encapsulated caffeine can be incorporated. The foods can be breakfast foods such as bagels, muffins, pancakes, pastries, doughnuts, dairy products, cereals, biscuits and the like, snacks such as granola bars, protein bars, cookies, chips, ice cream, popcorn and any other suitable snack, and/or other types of foods such as soups, sandwiches, vegetables, fruits, meats, dairy products, and the like which can be consumed to provide a burst of energy.

Preferably, the food product 14 is combined with encapsulated caffeine 12 to form an energy food. The encapsulated caffeine can be dispersed in a coating, such as an icing, dispersed in a filling material or the encapsulated caffeine can be dispersed throughout the entire food product.

Suitable oral tobacco and/or non-tobacco products include moist smokeless tobacco, tobacco pouch products and non-tobacco pouch products such as those described in commonly owned U.S. Pat. No. 7,980,251 issued Jul. 19, 2011 and U.S. Pat. No. 7,950,399 issued May 31, 2011, the entire content of each of which is incorporated herein by this reference thereto.

Figure 3:
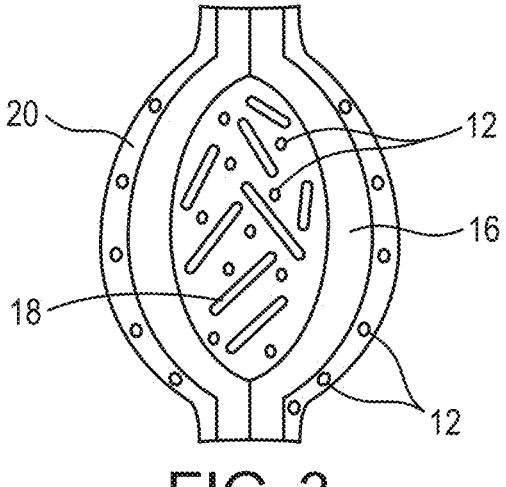
FIG. 3 is an illustration of an oral pouch product including encapsulated caffeine therein.

Preferably, the oral tobacco and/or non-tobacco products are pouch products including a porous pouch wrapper 16 containing botanical material 18 and optionally additives. Encapsulated caffeine 12 can be dispersed throughout the botanical material 18 as shown in FIG. 3. Alternatively, encapsulated caffeine can be dispersed throughout an outer coating or film 20, which is applied to a surface of the porous pouch wrapper 16.

The oral tobacco and/or non-tobacco pouch products are sized and configured to fit comfortably in a user's mouth, preferably between the cheek and gum. For example, the length of the oral pouch product can be up to about 5 cm, the width can be up to about 5 cm, and the height can be up to about 3 cm. In various embodiments, the oral pouch product 10 can have a length from about 1 cm to about 5 cm, from about 1 cm to about 4 cm, from about 1 cm to about 3 cm, or from about 1 cm to about 2 cm. The oral pouch product 10 can have a width from about 1 cm to about 5 cm, from about 1 cm to about 4 cm, from about 1 cm to about 3 cm, or from about 1 cm to about 2 cm. The oral pouch product 10 can have a height from about 10 mm to about 3 cm, from about 10 mm to about 2.5 cm, from about 10 mm to about 2 cm, from about 10 mm to about 1.5 cm, or from about 10 mm to about 1 cm.

The oral pouch product 10 may be formed in many shapes including, without limitation, spheres, rectangles, oblong shapes, crescent shapes, ovals, and cubes. In a preferred embodiment, the pre-portioned product is rectangular and weighs about 1.0 g to about 3.5 g, more particularly about 2.5 g to 3.0 g (e.g., about 2.6 g to about 2.9 g or about 2.7 g to about 2.8 g).

In the preferred embodiment, the compositions for human consumption can also include additives. Suitable additives for inclusion the in the compositions for human consumption include, without limitation, flavorants, vitamins, minerals, nutraceuticals, additional energizing agents, soothing agents, sweeteners, coloring agents, amino acids, antioxidants, preservatives, acidity regulators, viscosity adjusting agents, sensates and/or combinations thereof.

As used herein, the term "nutraceuticals" refers to any ingredient in foods that has a beneficial effect on human health. Nutraceuticals include particular compounds and/or compositions isolated from natural food sources and genetically modified food sources.

Optionally, the compositions for human consumption can include flavorants. Suitable flavorants include any flavorants commonly used in food and/or drinks. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as peppermint, spearmint, wintergreen, chocolate, licorice, citrus and fruit flavors, such as apple, peach, pear, cherry, plum, orange, lime, grape, mango, passion fruit, acai, pomegranate, pineapple, and grapefruit, gamma octalactone, vanillin, ethyl vanillin, butter, rum, coconut, almond, pecan, walnut, hazelnut, French vanilla, macadamia, sugar cane, maple, cassis, caramel, banana, malt, espresso, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, peanut oil, lemon oil, ginger oil, balsamic vinegar, rice wine vinegar and red wine vinegar. Other suitable flavors include vegetable flavors, such as tomato, carrot, spinach, broccoli, squash, onion, beet, turnip, parsnip, asparagus, pepper, leeks, rutabaga, fennel, zucchini, potato, and combinations thereof.

Preferably, the flavorants are added to the composition for human consumption in an amount of about 0.1% to about 50% by weight based on the weight of the composition for human consumption (e.g., about 1% to about 45%, about 2% to about 40%, about 5% to about 35%, about 10% to about 30%, or 15% to about 20%). The amount of flavorant added can depend on the flavorant used as some flavorants are more potent and/or concentrated than others and therefore can provide adequate flavoring in smaller amounts.

Preferably, the flavorants are added in the form of essential oils, encapsulated flavorants, coacervated flavorants, colloidal encapsulated flavorants, suspensions, and/or solutions. Alternatively, the flavorants can be added as dried powders, particles, and/or pieces.

Optionally, the compositions for human consumption can include at least one sweetener. Suitable sweeteners include, without limitation, monosaccharides, disaccharides, and polysaccharides, xylose, ribose, sucrose, maltose, mannitol, sorbitol, xylitol, fructose, glucose, mannose, sucralose, and combinations thereof. The amount of sweetener added to the energy drink or food can vary based on the sweetener and/or combination of sweeteners used. For example, sucralose may be added to the composition for human consumption in an amount of about 0.1% to about 3% by weight based on the weight of the composition for human consumption. More preferably, sucralose may be added to the composition for human consumption in an amount of about 0.5% to about 1.5% by weight based on the weight of the composition for human consumption. Also for example, sugar can be added in an amount of about 5% to about 25% by weight based on the weight of the composition for human consumption. More preferably, sugar is added in an amount of about 10% to about 20% by weight based on the weight of the composition for human consumption.

Optionally, soothing agents can be added to the composition for human consumption to provide a soothing sensation to the throat and oral cavity. Suitable soothing agents include, without limitation, chamomile, lavender, jasmine, and the like. The soothing agents can be included in an amount of about 0.1% to about 5% by weight based on the weight of the composition for human consumption.

Optionally, the composition for human consumption can also include additional energizing ingredients in addition to the caffeine complex. Suitable energizing ingredients include, without limitation, taurine, citicoline, and guarana. The energizing ingredients can be included in an amount of about 0.1% to about 5% by weight based on the weight of the composition for human consumption.

Optionally, the composition for human consumption can also include supplemental amounts of vitamins in addition to any present due to the inclusion of fruits and/or vegetables in the composition for human consumption. Suitable vitamins include, without limitation, vitamin A (retinol), vitamin D (cholecalciferol), vitamin E group, vitamin K group (phylloquinones and menaquinones), thiamine (vitamin B1), riboflavin (vitamin B2), niacin, niacinamide, pyridoxine (vitamin B6 group), folic acid, choline, inositol, vitamin B12 (cobalamins), PABA (para-aminobezoic acid), biotin, vitamin C (ascorbic acid), and mixtures thereof. The amount of vitamins incorporated into the composition for human consumption can be varied according to the type of vitamin and the intended consumer. For example, the amount of vitamins may be chosen so as to provide an amount less than or equal to the recommendations of the United States Department of Agriculture Recommended Daily Allowances.

Optionally, the composition for human consumption can include nutraceuticals. Suitable nutraceuticals include, without limitation, various phytonutrients derived from natural plants and genetically engineered plants. The nutraceuticals can be included in an amount of about 0.1% to about 5% by weight based on the weight of the composition for human consumption.

Optionally, the composition for human consumption can include a supplemental amount of minerals in addition to any included due to the inclusion of fruits and/or vegetables. Suitable minerals include, without limitation, calcium, magnesium, phosphorus, iron, zinc, iodine, selenium, potassium, copper, manganese, molybdenum, chromium, and mixtures thereof. The amount of minerals incorporated into the composition for human consumption can be varied according to the type of mineral and the intended consumer. For example, the amount of minerals may be formulated to include an amount less than or equal to the recommendations of the United States Department of Agriculture Recommended Daily Allowances.

Optionally, amino acids can also be included in the composition for human consumption. Suitable amino acids include, without limitation, the eight essential amino acids that cannot be biosynthetically produced in humans, including valine, leucine, isoleucine, lysine, threonine, tryptophan, methionine, and phenylalanine. Examples of suitable amino acids include the non-essential amino acids including alanine, arginine, asparagine, aspartic acid, cysteine, glutamic acid, glutamine, glycine, histidine, proline, serine, and tyrosine. The amino acids can be included in an amount of about 0.1% to about 5% by weight based on the weight of the composition for human consumption.

Optionally, the composition for human consumption can include various active agents having antioxidant properties that can delay the aging process. For example, the active ingredients that can be extracted from *Ginkgo biloba* include flavonoid glycosides ("ginkgoflavonoids"), such as (iso) quercitin, kaempferol, kaempferol-3-rhamnosides, isorhamnetin, luteolin, luteolin glycosides, sitosterol glycosides, and hexacyclic terpene lactones, referred to as "ginkgolides" or "bilobalides." The active ingredients that can be extracted from *Camellia sinensis*, such as green tea, include various "tea tannins," such as epicatechol, epigallocatechol, epigallocatechol gallate, epigallocatechol gallate, theaflavin, theaflavin monogallate A or B, and theaflavin digallate. The active ingredients that can be extracted from *Vaccinium myrtillus*, such as blueberry, include at least 15 different anthocyanosides, such as delphinidin, anthocyanosides, myrtin, epimyrtin, phenolic acids, glycosides, quercitrin, isoquercitrin, and hyperoside. The active ingredients that can be extracted from Vinis vitifera, such as grapes, include polyphenols, catechols, quercitrins, and resveratrols. The active ingredients that can be extracted from *Olea europensis*, such as the leaves of olive trees, include oleuropein. Many active ingredients identified from these and other plant sources associated with the neutralization of free radicals and useful for delaying the aging process are contemplated. The active ingredients of *Trifolium pratense*, such as purple clovers (i.e., common purple trefoils), include isoflavones or isoflavone glucosides, daidzein, genestein, formononentin, biochanin A, ononin, and sissostrin. The health-promoting properties of compounds derived from *Panax*, a genus that includes *Ginseng*, are well-established. These and other botanicals, botanical extracts, and bioactive compounds are contemplated.

Optionally, the composition for human consumption can also include preservatives to increase the shelf-life of the drink or food and/or prevent growth of bacteria, molds, fungus, and/or yeast. Moreover, the addition of preservatives may help maintain the color, flavor and/or texture of the composition for human consumption. Suitable preservatives for inclusion in the composition for human consumption include, without limitation, methyl paraben, propyl paraben, sodium propionate, citric acid, ascorbic acids, such as Vitamin C, sorbic acid alkali metal salts, such as potassium sorbate, benzoic acid alkali metal salts, such as sodium benzoate, and the like. The preservatives can be included in an amount sufficient to preserve the composition for human consumption and/or extend the shelf-life of the composition for human consumption to at least about 4 weeks or more. For example, the preservative can be included in the composition for human consumption in an amount of about 0.01% to about 1.0% by weight based on the weight of the composition for human consumption.

Optionally, the composition for human consumption, in particular an energy food or drink, includes at least one acidity regulator to maintain the pH of the energy drink or food below about 5, more preferably below about a pH of 4. Suitable acidity regulators for inclusion in the energy drinks or foods include, without limitation, ammonium hydroxide, potassium carbonate, sodium bicarbonate, sodium carbonate, potassium carbonate, calcium carbonate and combinations thereof. The at least one acidity regulator can be added in an amount sufficient to adjust the food or drink to a pH ranging from about 3 to about 5 prior to addition of the encapsulated caffeine thereto.

Not wishing to be bound by theory, it is believed that maintaining the pH of the energy drink or food at about 2 to about 5, preferably about 3.5 to about 4.5 results in the encapsulated caffeine not dissolving when dispersed in the energy drink. Since the dissolution of encapsulated caffeine is substantially prevented by maintaining the pH of the energy drink at about 2 to about 5, it is believed that the caffeine is substantially prevented from providing a bitter taste to the energy drink. However, once the energy drink is consumed and reach the consumers stomach, the pH of the stomach results in dissolution of the encapsulated caffeine so as to provide the energizing effects of caffeine without the bitter taste. Thus, the addition of an acidity regulator can help maintain the pH of the energy drink within a range that substantially prevents dissolution of encapsulated caffeine therein.

Optionally, the composition for human consumption can optionally include sensates such as capsaicin. Not wishing to be bound by theory, it is believed that the inclusion of sensates in the composition for human consumption provides a hot taste which can mask the bitterness of caffeine. Preferably, the composition for human consumption includes sensates in an amount sufficient to mask the bitter taste of caffeine. For example, the composition for human consumption can include sensates in an amount of about 0.1% to about 5% by weight based on the weight of the composition for human consumption.

Optionally, energy drinks or foods, such as soups, formed as described herein can include at least one viscosity increasing agent. Preferably, the at least one viscosity increasing agent is selected from the group consisting of pectin, alginate, starch, hydroxypropyl methyl cellulose, guar gum and combinations thereof. Also preferably, the at least one viscosity increasing agent is included in an amount ranging from about 0.5% by weight based on the weight of the composition for human consumption to about 5% by weight based on the weight of the composition for human consumption.

For example, an energy drink can be formed by adding encapsulated caffeine to water to form a dispersion. A viscosity increasing agent, such as alginate, can be then be added to the dispersion to aid in keeping the encapsulated caffeine suspended in the liquid base composition. Thus, delivery of the encapsulated caffeine is substantially consistent when the energy drink is consumed because the encapsulated caffeine is substantially evenly dispersed throughout the energy drink.

Optionally, at least one coloring agent can be added to the composition for human consumption in an amount effective to produce a desired color. The coloring agent can be selected from any pigment, natural food color or dyes suitable for human consumption. Preferably, the coloring agents are water-soluble coloring agents.

The composition for human consumption can be formed in any suitable manner. In the preferred embodiment, the encapsulated caffeine can be dispersed in the base composition by mixing the encapsulated caffeine and base composition, dispersing the encapsulated caffeine in the base composition, and in the case of energy foods, applying the encapsulated caffeine to a surface of the food. For example, the encapsulated caffeine can be applied as a coating to a food. Alternatively, the base composition can be mixed with the encapsulated caffeine such that the encapsulated caffeine is dispersed substantially throughout the composition for human consumption.

Moreover, the encapsulated caffeine can be formed by different methods and including different encapsulants so that the encapsulated caffeine dissolves in the stomach at differing rates so as to provide prolonged caffeine release. Additionally, the encapsulated caffeine could be formulated so as to provide delayed release of caffeine in the stomach. Thus, the composition including encapsulated caffeine could release caffeine immediately upon consumption (e.g., within about 30 seconds of consumption), at an intermediate time (e.g., about 30 seconds to about 5 minutes after consumption), or after an extended period of time (e.g., about 1 hour to 3 hours after consumption). In some embodiments, the composition can include encapsulated caffeine that releases immediately, intermediately and over an extended period of time to provide continued release of caffeine over a longer period of time. For example, the composition can include free caffeine that provides immediate release upon consumption, within about 5 minutes of consumption, and encapsulated caffeine which can release caffeine over an extended period of time, about 30 minutes or more after consumption.

The following examples are exemplary and are not meant to limit the embodiments disclosed herein.

Example 1

About 60 mL of water is mixed with a caffeine complex having a 1:1 molar ratio of caffeine and caffeic acid in an amount sufficient to deliver about 135 mg of active caffeine to form an energy drink. The resulting energy drink is less bitter than an energy drink containing 60 mL water and 135 mg of pure caffeine.

Example 2

About 60 ml of water is mixed with a caffeine complex having a 1:1 molar ratio of caffeine and malonic acid in an amount sufficient to deliver about 135 mg of active caffeine to form an energy drink. The resulting energy drink is less bitter than an energy drink containing 60 mL water and 135 mg of pure caffeine.

Example 3

About 60 mL of water is mixed with a caffeine complex having a 1:1 molar ratio of caffeine and oxalic acid in an amount sufficient to deliver about 135 mg of active caffeine to form an energy drink. The resulting energy drink is less bitter than an energy drink containing 60 mL water and 135 mg of pure caffeine.

Example 4

About 60 mL of water is mixed with a caffeine complex having a 1:1 molar ratio of caffeine and succinic acid in an amount sufficient to deliver about 135 mg of active caffeine to form an energy drink. The resulting energy drink is less bitter than an energy drink containing 60 mL water and 135 mg of pure caffeine.

Example 5

About 60 mL of water is mixed with a caffeine complex having a 1:1 molar ratio of caffeine and glutaric acid in an amount sufficient to deliver about 135 mg of active caffeine to form an energy drink. The resulting energy drink is less bitter than an energy drink containing 60 mL water and 135 mg of pure caffeine.

In this specification, the word "about" is often used in connection with numerical values to indicate that mathematical precision of such values is not intended. Accordingly, it is intended that where "about" is used with a numerical value, a tolerance of ±10% is contemplated for that numerical value.

While the foregoing describes in detail an energy drink or food including a caffeine complex and methods for forming a composition for human consumption including encapsulated caffeine with reference to a specific embodiment thereof, it will be apparent to one skilled in the art that various changes and modifications and equivalents to composition for human consumption and method may be employed, which do not materially depart from the spirit and scope of the invention.

We claim:

1. A method of making a composition, comprising:
   forming encapsulated caffeine from a caffeine complex that includes caffeine and an organic acid in a 1:1 molar ratio;
   dispersing the encapsulated caffeine throughout at least a portion of a base composition, the encapsulated caffeine being included in an amount sufficient to release 50 mg to 200 mg of caffeine when consumed; and
   adding at least one pH adjusting agent to the base composition to maintain a pH of the base composition within a range between 2 and 5, the base composition being an oral pouch product including a botanical filling material that is a tobacco material.

2. The method of claim 1, wherein the organic acid includes oxalic acid, malonic acid, maleic acid, succinic acid, adipic acid, caffeic acid, or combinations thereof.

3. The method of claim 1, wherein the organic acid includes oxalic acid, malonic acid, maleic acid, succinic acid, glutaric acid, glutamic acid, adipic acid, caffeic acid, or combinations thereof.

4. The method of claim 1, wherein the organic acid includes a monocarboxylic acid, a dicarboxylic acid, a multi-carboxylic acid or combinations thereof.

5. The method of claim 1, further comprising:
   adding one or more additives to the base composition, the one or more additives including at least one flavorant, at least one sweetener, at least one vitamin, at least one mineral, at least one nutraceutical, a viscosity increasing agent, at least one colorant, at least one preservative, or combinations thereof.

6. The method of claim 5, wherein the adding of the one or more additives includes adding the at least one flavorant in an amount ranging from 0.5% by weight based on a weight of the base composition to 25% by weight based on the weight of the base composition.

7. The method of claim 5, wherein the adding of the one or more additives includes adding the at least one sweetener in an amount ranging from 0.01% to 15% by weight based on a weight of the base composition.

8. The method of claim 7, wherein the adding of the one or more additives includes adding the at least one sweetener, the at least one sweetener including at least one of sucrose, fructose, dextrose, high fructose corn syrup, high maltose syrup, sugar alcohols, or a combination thereof.

9. The method of claim 1, wherein the adding of the at least one pH adjusting agent maintains the pH of the base composition within a range between 3.5 and 4.5.

10. The method of claim 1, wherein the dispersing of the encapsulated caffeine includes including an amount of the encapsulated caffeine sufficient to release 100 mg to 150 mg of caffeine during consumption.

11. The method of claim 1, wherein the forming of the encapsulated caffeine includes encapsulating the encapsulated caffeine to be released within 30 seconds of initial consumption, within 30 seconds to 5 minutes of initial consumption, or within 1 hour to 3 hours of initial consumption.

12. The method of claim 1, wherein the forming of the encapsulated caffeine includes encapsulating the encapsulated caffeine to be released within 1 hour to 3 hours of initial consumption.

13. A method of making a composition, comprising:

forming encapsulated caffeine from a caffeine complex that includes caffeine and an organic acid in a 1:1 molar ratio;

dispersing the encapsulated caffeine throughout at least a portion of a base composition, the encapsulated caffeine being included in an amount sufficient to release 50 mg to 200 mg of caffeine when consumed; and adding at least one pH adjusting agent to the base composition to maintain a pH of the base composition in an acidic range that is above a normal pH range of gastric acid in a human stomach to prevent a dissolution of the encapsulated caffeine prior to consumption, the base composition being an oral pouch product, the oral pouch product including a botanical filling material that is a tobacco material.

14. The method of claim 13, wherein the adding of the at least one pH adjusting agent maintains the pH of the base composition within a range between 2 and 5.

15. The method of claim 14, wherein the adding of the at least one pH adjusting agent maintains the pH of the base composition within a range between 3.5 and 4.5.

16. The method of claim 13, wherein the organic acid includes oxalic acid, malonic acid, maleic acid, succinic acid, glutaric acid, glutamic acid, adipic acid, caffeic acid, or combinations thereof.

17. The method of claim 13, further comprising:

adding one or more additives to the base composition, the one or more additives including at least one flavorant, at least one sweetener, at least one vitamin, at least one mineral, at least one nutraceutical, a viscosity increasing agent, at least one colorant, at least one preservative, or combinations thereof.

18. The method of claim 13, further comprising:

adding a viscosity increasing agent to the base composition to maintain the encapsulated caffeine in a dispersion within the base composition.

19. The method of claim 1, wherein the adding adds the at least one pH adjusting agent to maintain the pH of the base composition within a range between 2 and 5 to prevent a dissolution of the encapsulated caffeine prior to an exposure of the encapsulated caffeine to gastric acid in a human stomach during consumption of the encapsulated caffeine.

20. The method of claim 1, wherein the forming forms the encapsulated caffeine such that the organic acid is a mono-carboxylic acid, a dicarboxylic acid or a multi-carboxylic acid.

21. The method of claim 13, wherein the adding adds the at least one pH adjusting agent to maintain the pH of the base composition in the acidic range that is above the normal pH range of gastric acid in a human stomach to prevent the dissolution of the encapsulated caffeine, prior to an exposure of the encapsulated caffeine to gastric acid during consumption of the encapsulated caffeine.

22. The method of claim 13, wherein the forming forms the encapsulated caffeine such that the organic acid is a monocarboxylic acid, a dicarboxylic acid or a multi-carboxylic acid.

*     *     *     *     *